US006353061B1

United States Patent
Klee et al.

(10) Patent No.: US 6,353,061 B1
(45) Date of Patent: Mar. 5, 2002

(54) α, ω-METHACRYLATE TERMINATED MACROMONOMER COMPOUNDS

(75) Inventors: Joachim E. Klee, Radolfzell; Hans-Heinrich Hörhold; Frank Claussen, both of Jena, all of (DE)

(73) Assignee: Dentsply GmbH (DE)

(*) Notice: Subject to any disclaimer, the term of this patent is extended or adjusted under 35 U.S.C. 154(b) by 1532 days.

(21) Appl. No.: 08/627,328

(22) Filed: Apr. 4, 1996

Related U.S. Application Data

(63) Continuation of application No. 08/382,779, filed on Feb. 3, 1995, now abandoned, which is a continuation of application No. 08/067,774, filed on May 26, 1993, now abandoned.

(51) Int. Cl.$^7$ ............................................. C08F 283/00
(52) U.S. Cl. ................ 525/531; 433/228.1; 523/120; 523/401; 523/443; 523/444; 525/533; 525/922
(58) Field of Search ........................... 525/531, 530, 525/533, 922; 523/401, 443, 444, 120; 433/228.1

(56) References Cited

U.S. PATENT DOCUMENTS

| 150,262 A | 4/1874 | Slavin |
| 173,850 A | 2/1876 | Emde |
| 212,975 A | 4/1879 | Perkins et al. |
| 543,829 A | 7/1895 | Gurnee |
| 3,066,112 A | 11/1962 | Bowen ................ 260/1 |
| D195,391 S | 6/1963 | Pakison ................ D81/1 |
| 3,150,801 A | 9/1964 | Hamilton ................ 222/158 |
| 3,200,142 A | 8/1965 | Bowen ................ 260/286 |
| 3,256,226 A | 6/1966 | Fekete ................ 260/23.5 |
| 3,317,469 A | 5/1967 | Feichtinger et al. ........ 260/47 |
| 3,327,016 A | 6/1967 | Lee ................ 260/830 |
| 3,327,017 A | 6/1967 | Huang et al. ........ 260/844 |
| 3,466,259 A | 9/1969 | Jernigan ................ 260/37 |
| 3,503,128 A | 3/1970 | Boyd et al. ................ 32/15 |
| 3,539,533 A | 11/1970 | Lee, II et al. ........ 260/17 |
| 3,564,074 A | 2/1971 | Swisher et al. ........ 260/837 |
| 3,586,527 A | 6/1971 | Aronoff et al. ........ 117/93.31 |
| 3,595,969 A | 7/1971 | Shepherd et al. ........ 260/28.5 |
| 3,634,542 A | 1/1972 | Dowd et al. ........ 260/837 |
| 3,673,558 A | 6/1972 | Toepel et al. ........ 260/29.2 |

(List continued on next page.)

FOREIGN PATENT DOCUMENTS

| CA | 563464 | 9/1958 |
| CA | 817442 | 7/1969 |
| CA | 878004 | 8/1971 |
| CA | 878006 | 8/1971 |
| CA | 1107751 | 8/1971 |
| CA | 966500 | 4/1975 |
| CA | 983491 | 2/1976 |
| CA | 987044 | 4/1976 |
| CA | 995667 | 8/1976 |
| CA | 1018294 | 9/1977 |
| CA | 1030979 | 5/1978 |

(List continued on next page.)

OTHER PUBLICATIONS

Lal et al; Journal of Polymer Science: vol. XXIV, pp. 75–84 (1957) New Polymerization Catalysts for Methyl Methacrylate.

Beaunez et al: Journal of Polymer Science: Part A: Polymer Chemistry, vol. 32, pp. 1459–1469 (1994).

Antonucci et al; Journal of Dental Research 58 (9), pp. 1887–1899, Sep. 1979; New Initiator Systems for Dental Resins based on Ascorbic Acid.

Chemistry Abstract 115 (1991) 78952z and Chemistry Abstract 115 (1991) 78973g.

Klee et al, Polymer Bulletin 27 (1992) ; pp. 511–517.

Chemical Abstract, vol. 89, No18, Oct. 30, 1978, Columbis OH, US; Abstract No. 148211C; p. 71, Col. 2; abstract & Lakokras Mater. IKH, Primen., No. 4, 1978, p. 50–52.

(List continued on next page.)

Primary Examiner—Robert Dawson
(74) Attorney, Agent, or Firm—Dale R. Lovercheck; James B. Bieber

(57) ABSTRACT

A α,ω-methacrylate terminated epoxide-carboxylic acid macromonomer compound formed by reaction of at least one diepoxide, at least one dicarboxylic acid and at least one unsaturated mono-carboxylic acid and having the general formula 1:

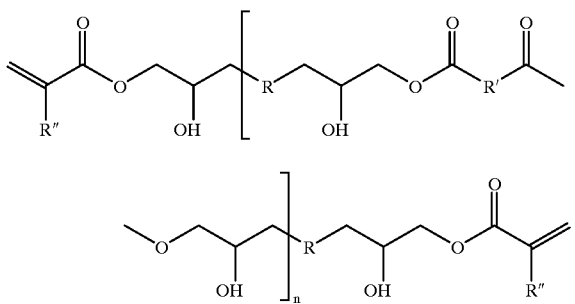

wherein R is an aromatic moiety formed from a diepoxide

R' is a substituted or unsubstituted aliphatic, araliphatic, cycloaliphatic or aromatic moiety formed from a dicarboxylic acid, R" is hydrogen, a substituted or unsubstituted aliphatic, araliphatic, aromatic or cycloaliphatic moiety formed from a mono-carboxylic acid, and n is an integer from 1 to 20.

13 Claims, No Drawings

U.S. PATENT DOCUMENTS

| | | | |
|---|---|---|---|
| 3,709,866 A | 1/1973 | Waller | 260/27 |
| 3,742,949 A | 7/1973 | Hill | 128/218 |
| 3,754,054 A | 8/1973 | Khnura et al. | 260/860 |
| 3,769,336 A | 10/1973 | Lee, Jr. et al. | 260/486 |
| 3,815,239 A | 6/1974 | Lee, Jr. et al. | 32/15 |
| 3,835,090 A | 9/1974 | Gander et al. | 260/42.15 |
| 3,845,009 A | 10/1974 | Gander | 260/42.15 |
| 3,853,962 A | 12/1974 | Gander | 260/486 |
| 3,882,187 A | 5/1975 | Takiyama et al. | 260/835 |
| 3,889,385 A | 6/1975 | Dougherty | 32/12 |
| 3,926,906 A | 12/1975 | Lee, II et al. | 260/42.53 |
| 3,971,765 A | 7/1976 | Green et al. | 260/78 |
| 3,973,972 A | 8/1976 | Muller | 106/39.7 |
| 3,980,483 A | 9/1976 | Nishikubo et al. | 96/115 |
| 4,002,669 A | 1/1977 | Gross et al. | 260/486 |
| 4,051,195 A | 9/1977 | McWhorter | 260/837 |
| 4,081,492 A | 3/1978 | Traenckner et al. | 260/837 |
| 4,097,569 A | 6/1978 | Waters | 264/255 |
| 4,097,994 A | 7/1978 | Reaville et al. | 32/15 |
| 4,098,735 A * | 7/1978 | Tobias | 525/533 |
| 4,100,045 A | 7/1978 | Bogan et al. | 204/159.16 |
| 4,135,868 A | 1/1979 | Schainholz | 422/310 |
| 4,141,865 A * | 2/1979 | Bogan | 525/531 |
| 4,150,012 A | 4/1979 | Joos | 260/42.15 |
| 4,177,563 A | 12/1979 | Schmitz-Josten et al. | 433/228 |
| 4,182,035 A | 1/1980 | Yamauchi et al. | 433/228 |
| 4,182,833 A | 1/1980 | Hicks | 528/120 |
| 4,197,390 A | 4/1980 | Jackson | 528/115 |
| 4,220,582 A * | 9/1980 | Orlowski et al. | 523/116 |
| 4,229,376 A | 10/1980 | Rogier | 260/563 P |
| 4,253,830 A | 3/1981 | Kazen et al. | 433/77 |
| 4,255,468 A | 3/1981 | Olson | 427/137 |
| 4,256,457 A | 3/1981 | Behring | 433/77 |
| 4,284,742 A | 8/1981 | Bowerman, Jr. et al. | 525/329 |
| 4,293,074 A | 10/1981 | Dunsky | 206/572 |
| 4,296,004 A | 10/1981 | Rogier | 260/18 EP |
| 4,308,085 A | 12/1981 | Horhold et al. | 156/330 |
| 4,362,889 A * | 12/1982 | Bowen | 525/531 |
| 4,368,889 A | 1/1983 | Reker, Jr. | 273/243 |
| 4,383,826 A | 5/1983 | Butler et al. | 433/228 |
| 4,383,879 A | 5/1983 | Le Du et al. | 156/307 |
| 4,384,853 A | 5/1983 | Welsh | 433/90 |
| 4,391,590 A | 7/1983 | Dougherty | 433/90 |
| 4,405,766 A | 9/1983 | Bertram et al. | 525/507 |
| 4,406,625 A | 9/1983 | Orlowski et al. | 433/228 |
| 4,413,105 A * | 11/1983 | Koenig | 525/531 |
| 4,431,421 A | 2/1984 | Kawahara et al. | 433/228 |
| 4,446,246 A | 5/1984 | McGinniss | 502/155 |
| 4,467,079 A | 8/1984 | Hechenberger et al. | 526/90 |
| 4,514,342 A | 4/1985 | Billington et al. | 260/952 |
| 4,515,634 A | 5/1985 | Wu et al. | 106/35 |
| 4,524,161 A | 6/1985 | Feuerhahn | 523/414 |
| 4,541,992 A | 9/1985 | Jerge et al. | 422/300 |
| 4,547,531 A | 10/1985 | Waknine | 523/116 |
| 4,548,689 A | 10/1985 | Sakashita et al. | 204/159.23 |
| 4,557,848 A | 12/1985 | Sung et al. | 252/51.5 |
| 4,569,662 A | 2/1986 | Dragan | 433/89 |
| 4,579,904 A | 4/1986 | Orlowski et al. | 524/554 |
| 4,595,734 A * | 6/1986 | O'Hearn | 525/922 |
| 4,643,303 A | 2/1987 | Arp et al. | 206/370 |
| 4,714,571 A | 12/1987 | Schornick et al. | 528/103 |
| 4,714,751 A | 12/1987 | Schornick et al. | 528/103 |
| 4,758,643 A | 7/1988 | Tanaka et al. | 526/279 |
| 4,767,326 A | 8/1988 | Bennett et al. | 433/90 |
| 4,774,063 A | 9/1988 | Runnells | 422/297 |
| 4,781,921 A | 11/1988 | Smith et al. | 424/81 |
| 4,789,620 A | 12/1988 | Sasaki et al. | 430/280 |
| 4,806,381 A | 2/1989 | Engelbrecht et al. | 427/2 |
| 4,816,495 A | 3/1989 | Blackwell et al. | 522/14 |
| 4,816,528 A * | 3/1989 | Dervan et al. | 525/533 |
| 4,854,475 A | 8/1989 | Riihimaki et al. | 220/337 |
| 4,863,993 A | 9/1989 | Montgomery | 524/854 |
| 4,866,146 A | 9/1989 | Janda et al. | 526/213 |
| 4,872,936 A | 10/1989 | Engelbrecht | 156/307.3 |
| 4,874,799 A | 10/1989 | Hung et al. | 522/96 |
| 4,883,899 A | 11/1989 | Muramoto et al. | 560/14 |
| 4,918,136 A | 4/1990 | Kawaguchi et al. | 524/751 |
| 4,931,096 A | 6/1990 | Fujisawa et al. | 106/35 |
| 4,936,775 A * | 6/1990 | Bennett | 433/220 |
| 4,950,697 A | 8/1990 | Chang et al. | 523/116 |
| 4,959,199 A | 9/1990 | Brewer | 422/300 |
| 4,963,093 A | 10/1990 | Dragan | 433/90 |
| 4,964,911 A | 10/1990 | Ibsen et al. | 106/35 |
| 4,969,816 A | 11/1990 | Drumm | 433/90 |
| 4,985,198 A | 1/1991 | Hirasawa et al. | 560/130 |
| 4,985,516 A | 1/1991 | Sakashita et al. | 526/196 |
| D315,956 S | 4/1991 | Dragan | D24/14 |
| 5,006,066 A | 4/1991 | Rouse | 433/77 |
| 5,052,927 A | 10/1991 | Discko, Jr. | 433/90 |
| 5,083,921 A | 1/1992 | Dragan | 433/90 |
| 5,100,320 A | 3/1992 | Martin et al. | 433/90 |
| 5,106,301 A | 4/1992 | Miyahara et al. | 433/214 |
| 5,108,287 A | 4/1992 | Yee et al. | 433/77 |
| 5,122,057 A | 6/1992 | Discko, Jr. | 433/90 |
| 5,129,825 A | 7/1992 | Discko, Jr. | 433/90 |
| 5,137,990 A | 8/1992 | Corley | 525/530 |
| 5,151,479 A | 9/1992 | Mukai et al. | 526/277 |
| 5,165,890 A | 11/1992 | Discko, Jr. | 433/90 |
| 5,166,117 A | 11/1992 | Imai et al. | 502/169 |
| 5,172,810 A | 12/1992 | Brewer | 206/369 |
| 5,173,273 A | 12/1992 | Brewer | 422/300 |
| 5,189,077 A | 2/1993 | Kerby | 523/116 |
| 5,204,398 A * | 4/1993 | Cohen et al. | 523/176 |
| 5,210,157 A | 5/1993 | Schutyser et al. | 525/502 |
| 5,215,726 A | 6/1993 | Kudla et al. | 422/297 |
| 5,217,372 A | 6/1993 | Truocchio | 433/215 |
| 5,235,008 A | 8/1993 | Hefner, Jr. et al. | 525/529 |
| 5,236,362 A | 8/1993 | Cohen et al. | 433/228.1 |
| 5,252,629 A | 10/1993 | Imai et al. | 523/118 |
| 5,267,859 A | 12/1993 | Discko, Jr. | 433/89 |
| 5,279,800 A | 1/1994 | Berr, Jr. | 422/300 |
| 5,284,632 A | 2/1994 | Kudla et al. | 422/297 |
| 5,294,413 A | 3/1994 | Riihimaki et al. | 422/297 |
| 5,322,440 A | 6/1994 | Steele | 433/90 |
| 5,324,273 A | 6/1994 | Discko, Jr. | 604/240 |
| 5,340,551 A | 8/1994 | Berry, Jr. | 422/300 |
| 5,346,677 A | 9/1994 | Risk | 422/297 |
| 5,360,877 A | 11/1994 | Hwang et al. | 525/423 |
| D353,673 S | 12/1994 | Discko, Jr. et al. | D24/152 |
| 5,384,103 A | 1/1995 | Miller | 422/310 |

FOREIGN PATENT DOCUMENTS

| | | |
|---|---|---|
| CA | 1099848 | 4/1981 |
| CA | 1100990 | 5/1981 |
| CA | 1107293 | 8/1981 |
| CA | 1115289 | 12/1981 |
| CA | 1131827 | 9/1982 |
| CA | 1140939 | 2/1983 |
| CA | 1151667 | 8/1983 |
| CA | 1153391 | 9/1983 |
| CA | 1155141 | 10/1983 |
| CA | 1175196 | 9/1984 |
| CA | 1183144 | 2/1985 |
| CA | 1185982 | 4/1985 |
| CA | 1200555 | 2/1986 |
| CA | 1202749 | 4/1986 |
| CA | 1210777 | 9/1986 |
| CA | 1219990 | 3/1987 |
| CA | 1227202 | 9/1987 |
| CA | 1235423 | 4/1988 |
| CA | 1242213 | 9/1988 |

| | | |
|---|---|---|
| CA | 1248126 | 1/1989 |
| CA | 1258465 | 8/1989 |
| CA | 2002017 | 5/1990 |
| CA | 1270846 | 6/1990 |
| CA | 2005912 | 6/1990 |
| CA | 2006431 | 6/1990 |
| CA | 2006432 | 6/1990 |
| CA | 2006433 | 6/1990 |
| CA | 2006434 | 6/1990 |
| CA | 2004624 | 7/1990 |
| CA | 2026009 | 7/1990 |
| CA | 1272735 | 8/1990 |
| CA | 2008895 | 8/1990 |
| CA | 2009471 | 8/1990 |
| CA | 2012824 | 9/1990 |
| CA | 2014027 | 10/1990 |
| CA | 2014359 | 10/1990 |
| CA | 1276168 | 11/1990 |
| CA | 1276648 | 11/1990 |
| CA | 1277070 | 11/1990 |
| CA | 2054747 | 11/1990 |
| CA | 2010210 | 12/1990 |
| CA | 2018728 | 12/1990 |
| CA | 2019410 | 12/1990 |
| CA | 2054710 | 12/1990 |
| CA | 2054757 | 12/1990 |
| CA | 1281734 | 3/1991 |
| CA | 2026467 | 3/1991 |
| CA | 1283121 | 4/1991 |
| CA | 1283663 | 4/1991 |
| CA | 2027887 | 4/1991 |
| CA | 2042587 | 4/1991 |
| CA | 2028728 | 5/1991 |
| CA | 2032556 | 6/1991 |
| CA | 2033405 | 7/1991 |
| CA | 2035650 | 8/1991 |
| CA | 2026417 | 9/1991 |
| CA | 2038332 | 9/1991 |
| CA | 1290766 | 10/1991 |
| CA | 2045762 | 12/1991 |
| CA | 2046373 | 1/1992 |
| CA | 1296015 | 2/1992 |
| CA | 2049725 | 3/1992 |
| CA | 2061230 | 8/1992 |
| CA | 2061539 | 8/1992 |
| CA | 2041828 | 11/1992 |
| CZ | 227 363 | 1/1984 |
| DE | 1 003 448 | 8/1958 |
| DE | 2 126 419 | 12/1971 |
| DE | 2126419 | 12/1971 |
| DE | 141 667 | 5/1980 |
| DE | 154 945 | 6/1982 |
| DE | 209 358 | 4/1984 |
| DE | 208 365 | 5/1984 |
| DE | 214 381 | 10/1984 |
| DE | 229 140 | 10/1985 |
| DE | 244 748 | 4/1987 |
| DE | 35 36 076 | 4/1987 |
| DE | 35 36 077 | 4/1987 |
| DE | 248 598 | 8/1987 |
| DE | 261 365 | 10/1988 |
| DE | 277 078 | 3/1990 |
| DE | 277 689 | 4/1990 |
| DE | 279 667 A1 | 6/1990 |
| DE | 279 667 | 8/1990 |
| DE | 295 758 | 11/1991 |
| DE | 41 41 174 | 6/1992 |
| DE | 41 09 048 | 9/1992 |
| DE | 42 17 761 | 2/1993 |
| EP | 037 759 | 10/1981 |
| EP | 120 559 | 1/1983 |
| EP | 0 104 491 | 4/1984 |
| EP | 104 491 | 4/1984 |
| EP | 115 410 | 4/1984 |
| EP | 115 948 | 8/1984 |
| EP | 188 752 | 12/1984 |
| EP | 0 188 752 | 7/1986 |
| EP | 212 193 | 3/1987 |
| EP | 219 058 | 4/1987 |
| EP | 277 413 | 10/1988 |
| EP | 356 868 | 3/1990 |
| GB | 2 045 269 | 10/1980 |
| GB | 2 199 839 | 7/1988 |
| JP | 3-27308 | 6/1989 |
| SU | 52106 | 7/1937 |
| SU | 311 637 | 8/1971 |
| SU | 311 638 | 8/1971 |
| SU | 349 396 | 9/1972 |
| SU | 545 353 | 2/1977 |
| SU | 549 150 | 3/1977 |
| SU | 1 050 706 | 4/1982 |
| SU | 1 510 131 | 11/1986 |
| WO | 90/15083 | 12/1990 |
| WO | 90/15084 | 12/1990 |
| WO | 91/03502 | 3/1991 |
| WO | 93/10176 | 5/1993 |

OTHER PUBLICATIONS

Dusek et al; American Chemical Society (1984) Transesterification and Gelation of Polyhydroxy Esters Formed from Diepoxides and Dicarboxylic Acids.

Hartel et al; (Nov. 1984) Zur Synthese linearer Additionspolymere aus Diandiglycidether und Dicarbonsauren.

Klee; Acta Polymer 44, 163–167 (1993); Synthesis and investigation of α, w–methacryloyl poly (epoxide–carboxylic acid and α, w–methacryloyl poly (epoxide–phenol)—macromonomers.

J. Klee et al, Acta Polymer 42 (1991) 17–20.

Fukushima et al; Dental Materials Journal 4(1) : pp. 33–39 (1985) : Application of Functional Monomers for Dental Use (Part 9) Sysntheses of Succinoxy Methacrylates and Their Adhesion to Polished and Etched Tooth Surfaces.

Lin et al; Journal of Polymer Science; Part A: Polymer Chemistry, vol. 30, 1941–1951 (1992).

Allard et al; Journal of Polymer Science: Polymer Chemistry Edition, vol. 22, 3827–3842 (1984).

Hage et al; American Chemical Society (1986) Poly (acrylourethane)—Polyepoxide Semi—interpenetrating Networks Formed by Electron–Beam Curing.

Dubuisson et al; Rheol. Acta 20, 463–470 (1981).

Klee; Acta Polymer., 45, 73–82 (1994) Telechelic prepolymers and macromonomers by step growth processes.

John Wiley & Sons; Encyclopedia of Polymer Science and Engineering, vol. 8, Identification to Lignin.

Rot et al, Chemical Abstract, vol. 89, No. 18, Oct. 30, 1978, Columubs, Ohio, US; Abstract No. 148211c; p. 71, col. 2; *abstract* & LAKOKRAS MATER. IKH. PRIMEN., No. 4, pp. 50–52, 1978.

Dusek et al, Transesterification & Gelation of Polyhydroy Esters, Formed from Diepoxides & Dicarboxylic Acids, Amer. Chem. Societym 1984.

Hartel et al, Zur Synthese linearer Additionspolymere aus Diandiglycidether und Dicarbonsauren, (11/84).

Klee et al, Synthesis and investigation of α, ω–methacryloyl poly (epoxide–carboxylic acid and α, ω–methacryloyl poly (epoxide–phenol) –macromonomers, Acta Polymer 44, 163–167 (1993).

Klee et al., Polym Bull. 27 (1992) ; 511–517.

J. Klee et al., Acta Polym. 42 (1991) 17–20.

Chemical Abstract, vol. 89, No. 18, Oct. 30, 1978, Columbus, Ohio, US; Abstract No. 148211c; p. 71, col. 2; *abstract* & LAKOKRAS MATER. IKH. PRIMEN., No. 4, 1978, pp. 50–52.

Synthesis and investigation of a,w–methacryloyl poly (epoxide–carboxylic) acid and a,w–methacryloyl poly (epoxide–phenol) –macromonomers Acta Polymer 44, 163–167 (1993).

* cited by examiner

α, ω-METHACRYLATE TERMINATED MACROMONOMER COMPOUNDS

This is a continuation of application Ser. No. 08/382,779, filed Feb. 3, 1995, now abandoned which is a continuation of U.S. patent application Ser. No. 08/067,774 filed May 26, 1993, now abandoned.

The invention relates to compounds having repetitive units of α,ω-methacrylate terminated macromonomer epoxide-carboxylic acid. Synthesis of such compounds is carried out by a two-step reaction or by simultaneous polymerization of diepoxides, dicarboxylic acids and unsaturated monocarboxylic acids. These compounds are useful as dental adhesives, dental cements, dental restoratives and dental luting materials.

α,ω-methacrylate terminated epoxide-amine macromonomers recently described in patent application (DD 279667) are not comparable to the α,ω-methacrylate epoxide-carboxylic acid macromonomers of the present invention. Nor is the synthesis of the α,ω-methacrylate terminated epoxide carboxylic acid macromonomers of the present invention comparable to the synthesis of amine-macromonomers, because carboxylic acids react at higher temperatures with epoxides than do amines (see Houben-Weyl Bd 14/2, S. 499ff). At such high reaction temperatures there is concern that the polymerization of the unsaturated monocarboxylic acid may occur. M. Fedkte et al, in Plaste and Kautschuk 31 (1984) 405; K. Dusek, L. Matejka, Amer. Chem. Soc. 1984, 15, disclose reaction of epoxide-carboxylic acid to form insoluble network polymers caused by side reactions of epoxides and hydroxylic groups wherein R is an aromatic diepoxide moiety. The synthesis of α,ω-methacrylate terminated epoxide carboxylic acid macromonomers in accordance with the present invention is surprising.

As used herein "(Meth)acrylic acid" is understood to mean acrylic and methacrylic acids.

BRIEF SUMMARY OF THE INVENTION

The invention provides α,ω-methacrylate terminated epoxide-carboxylic acid macromonomer compounds formed by reaction of at least one diepoxide, at least one dicarboxylic acid and at least one unsaturated monocarboxylic acid and having the general formula 1:

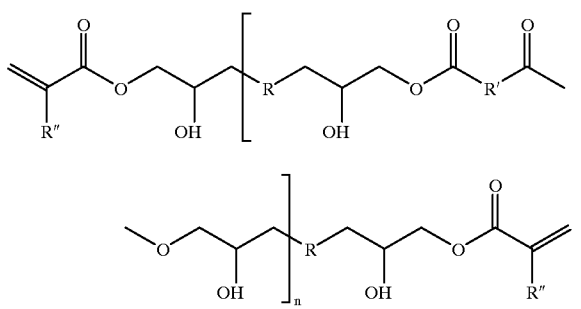

wherein R is an aromatic moiety formed from a diepoxide,
R' is a substituted or unsubstituted aliphatic, araliphatic, cycloaliphatic or aromatic moiety formed from a dicarboxylic acid,
R' is hydrogen, a substituted or unsubstituted aliphatic, araliphatic, aromatic or cycloaliphatic moiety formed from a mono-carboxylic acid, and n an integer from 1 to 20.

DETAILED DESCRIPTION OF THE INVENTION

The invention provides α,ω-methacrylate terminated epoxide-carboxylic acid macromonomer compounds within the scope of general formula (1):

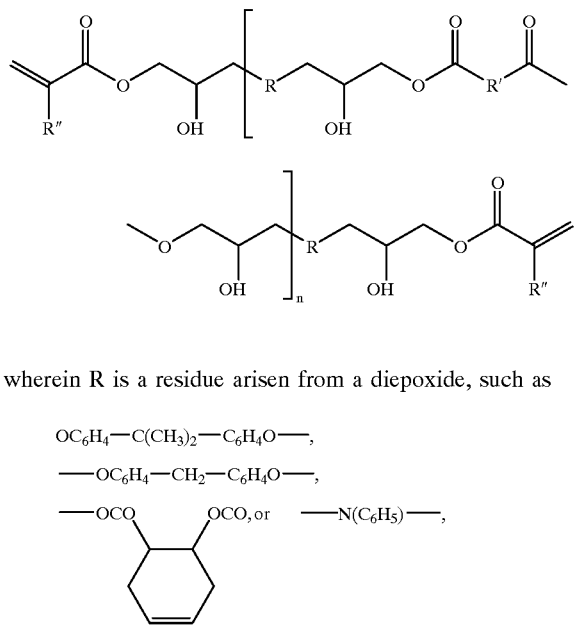

wherein R is a residue arisen from a diepoxide, such as

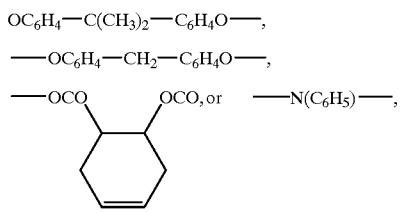

R' is a difunctional substituted or unsubstituted aliphatic, araliphatic, cycloaliphatic or aromatic residue, such as
$CH_2CH_2-$, $-CH_2CH_2CH_2CH_2$, $-CH_2-(CH_2)_8-$, $C_6H_4-$, or $-C_6H_{10}-$, R' is hydrogen or a monofunctional substituted or unsubstitued aliphatic, araliphatic, aromatic or cycloaliphatic moiety, but preferably $CH_3$, and n is an integer from 1 to 20. Compounds within the scope of general formula 1 are prepared by reaction of diepoxides, dicarboxylic acids and unsaturated mono-carboxylic acids. Preferably this reaction is carried out in the presence of catalysts and/or accelerators neat or in solvents such as tetrahydrofuran, toluene, or triethyleneglycoldimethacrylate at temperatures between 60 to 150° C.

In accordance with the invention are provided compositions which include at least one compound within the scope of general formula 1 and at least one polymerizable low molecular weight oligomer having a moiety formed from at least one diepoxide and at least one monocarboxylic acid.

(Meth)acrylic acid is a preferred monocarboxylic acid used for the synthesis of α,ω-methacrylate terminated epoxide-carboxylic acid macromonomers of formula 2:

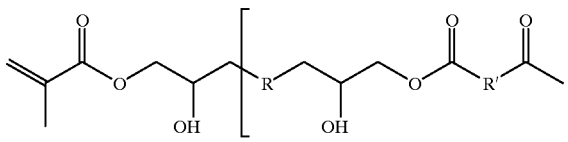

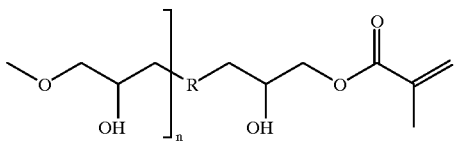

wherein R is a residue arisen from a diepoxide, such as $OC_6H_4-C(CH_3)_2-C_6H_4O-$, $-OC_6H_4-CH_2-C_6H_4O-$,

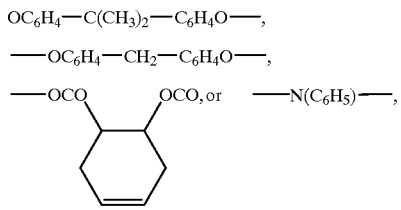

R' is a difunctional substituted or unsubstituted aliphatic, araliphatic, cycloaliphatic or aromatic residue, such as $CH_2CH_2-$, $-CH_2CH_2CH_2CH_2-$, $-CH_2-(CH_2)_8-$, $C_6H_4-$, or $-C_6H_{10}-$, n is an integer from 1 to 20.

The α,ω-methacrylate terminated epoxide-carboxylic acid-macromonomers are preferably prepared in two steps. In the first step a prepolymer is formed by reaction of diepoxides with dicarboxylic acids. Then these prepolymers are terminated by reaction with an unsaturated monocarboxylic acid. The reactions in these steps may preferably occur simultaneously. Preferably tetrahydrofuran, dioxane, and/or toluene, are used as solvents for these reactants.

Polymerizable diluents such as triethyleneglycolbismethacrylate, diethyleneglycolbismethacrylate, dioxolanbismethacrylate, vinyl-, vinylene- or vinylidene-compounds, acrylate or methacrylate substituted spiroorthoesters, bisphenol-A-bis (3-methacrylato-2-hydroxypropyl) ether (hereinafter ethyoxylated Bis-GMA) are preferably used as solvents for the synthesis of macromonomers in accordance with the invention. Thus polymerizable diluents preferably became part of a macromonomer containing solution to provide a useful function such as reduced viscosity desirable to compound dental composites for restorative dentistry.

The α,ω-methacrylate terminated epoxide-carboxylic acid macromonomers within the scope of general formulas 1 and 2 of the invention are preferably polymerized using photochemical, radical initiated, and other methods of polymerization, including methods known in the art to accelerate the polymerization of methacrylate monomers. The polymers show good mechanical properties, good adhesion to metals, glass and ceramics. Furthermore they show a relatively low water absorption and especially low shrinkage during the polymerization.

Compounds within the scope of general formula 1 are useful as dental adhesives, and are preferably used in dental compositions which include a self cure catalyst such as benzoyl peroxide. Polymerizable dental composite compositions in accordance with the invention preferably include at least one compound within the scope of general formula 1 and a filler, such as organic polymer particles and/or inorganic particles.

EXAMPLE 1

6.808 g (20.00 mmol) bisphenol-A diglycidyl ether, 1.462 g (10.00 mmol) adipic acid and 0.091 g triethylbenzylammoniumchloride are dissolved in one another and stirred and heated quickly to 150° C. (2–5 minutes) and reacted for 1 hour at 90° C. to form a reaction mixture. Then 0.009 g hydroquinone and 1.722 g (20.00 mmol) methacrylic acid are added to the reaction mixture, stirred and reacted for four hours at 90° C. The methacrylate terminated macromonomer obtained is soluble in organic solvents including chloroform, DMF and THF, and has $M_n$(vpo) of 1050 g/mol, $T_g$ of 13.9° C. the formula ($C_{56}H_{70}O_{16}$) 999.17 g/mol with a calculated C. of 67.32 and H of 7.06 and a found C of 67.37 and H of 7.34.

EXAMPLE 2

6.808 g (20.00 mmol) bisphenol-A diglycidyl ether, 2.023 g (10.00 mmol) sebacic acid and 0.091 g triethylbenzylammoniumchloride were stirred while heating to 150° C. (2–5 minutes) and allowed to react for 1 hour at 90° C. to form a reaction mixture. Then 0.009 g hydroquinone and 1.722 g (20.00 mmol) methacrylic acid are added to the reaction mixture, dissolved with stirring and reacted for four hours at 90° C. The methacrylate terminated macromonomer obtained is soluble in organic solvents including chloroform, DMF and THF. It has $M_n$(vpo) of 1130 g/mol, $T_g$ of 6.9° C. and formula ($C_{60}H_{78}O_{16}$) 1055.27 g/mol.

EXAMPLE 3

6.808 g (20.00 mmol) bisphenol-A diglycidyl ether, 2.222 g (10.00 mmol) 3,6,9-trioxaundecane dicarboxylic acid and 0.091 g triethylbenzylammonium chloride are stirred while heating to 150° C. (2–5 minutes) and reacted for 1 hour at 90° C. to form a reaction mixture. Then 0.009 g hydroquinone and 1.722 g (20.00 mmol) methacrylic acid are added to the reaction mixture stirred and reacted for further four hours at 90° C. The methacrylate terminated macromonomer obtained is soluble in organic solvents including chloroform, DMF and THF. It has $M_n$(vpo) of 1090 g/mol, $T_g$ of 14.4° C. and the formula ($C_{58}H_{74}O_{19}$) 1075.21 g/mol.

EXAMPLE 4

13.616 g (40.00 mmol) bisphenol-A diglycidyl ether, 2.924 g (20.00 mmol) adipic acid, 3.444 g (40.00 mmol) methacrylic acid, 5.052 g triethyleneglycoldimethacrylate, 0.182 g triethylbenzylammoniumchloride and 0.040 g 2,6-di-tert-butyl-p-cresol are reacted for four hours at 90° C. The methacrylate terminated macromonomer obtained is soluble in organic solvents including chloroform, DMF and THF. Its IR-spectrum has absorption at 1720 cm$^{-1}$ indicating ester groups and no absorption of epoxide groups at 915 and 3050 cm$^{-1}$.

EXAMPLE 5

13.616 g (40.00 mmol) bisphenol-A diglycidyl ether, 3.323 g (20.00 mmol) isophthalic acid, 3.444 g (40.00 mmol) methacrylic acid, 5.052 g triethyleneglycoldimethacrylate, 0.182 g triethylbenzylammoniumchloride and 0.040 g 2,6-di-tert-butyl-p-cresol are reacted for four hours at 90° C. The methacrylate terminated macromonomer obtained is soluble in organic solvents including chloroform, DMF and THF. Its IR-spectrum has absorption at 1720 cm$^{-1}$ indicating ester groups and no absorption of epoxide groups at 915 and 3050 cm$^{-1}$.

EXAMPLE 6

20.425 g (60.00) mmol) bisphenol-A diglycidyl ether, 5.848 g (40.00 mmol) adipic acid, 3.444 g (40.00 mmol)

methacrylic acid, 7.430 triethyleneglycoldimethacrylate, 0.246 g triethylbenzylammoniumchloride and 0.060 g 2,6-di-tert.-butyl-p-cresol are reacted for four hours at 90° C. The methacrylate terminated macromonomer obtained is soluble in organic solvents such as chloroform, DMF and THF. Its IR-spectrum has absorption at 1720 cm$^{-1}$ and no absorption of epoxide groups at 915 and 3050 cm$^{-1}$ was observed.

Composite Material

EXAMPLE 7

13.616 g (40.00 mmol) bisphenol-A diglycidyl ether, 2.924 g (20.00 mmol) adipic acid, 3.444 g (40.00 mmol) methacrylic acid, 5.052 g triethyleneglycoldimethacrylate, 0.182 g triethylbenzylammoniumchloride and 0.040 g 2,6-di-tert-butyl-p-cresol are reacted for four hours at 90° C. to form a macromonomer containing liquid. The methacrylate terminated macromonomer obtained is soluble in organic solvents including chloroform, DMF and THF. Its IR-spectrum has absorption at 1720 cm$^{-1}$ indicating ester groups and no absorption of epoxide groups at 915 and 3050 cm$^{-1}$. 24 g of the macromonomer containing liquid is mixed with 75 g of APH glass, 0.5 g of propamine and 0.5 g of camphorquinone to form a polymerizable dental composite forming material. Visible light is directed onto this dental composite forming material which polymerizes to form a polymeric dental composite having a shrinkage of 1.27% a compressive strength of 129.8 MPa, a compressive modulus of 1505.0 MPa, a flexural strength of 52.6 MPa, and a diametral tensile strength of 34.6 MPa

EXAMPLE 8

51.060 g (0.15 mol) bisphenol-A diglycidyl ether, 10.110 g (0.05 mol) sebacic acid, 17.220 g (0.20 mol) methacrylic acid, 0.402 g triethylbenzylammoniumchloride and 0.164 g 2,6-di-tert.-butyl-p-cresol were reacted for four hours at 90° C. The methacrylate terminated macromonomer obtained is soluble in organic solvents including chloroform, DMF and THF. Its IR-spectrum has absorption at 1720 cm$^{-1}$ indicating ester groups and no absorption of epoxide groups at 915 and 3050 cm$^{-1}$.

$M_n$(calc.)=783.9 g/mol, $M_n$(vpo)=750 g/mol

Dental Restorative

EXAMPLE 9

15.36 g of the macromonomer formed as described in Example 6, 8.64 g of triethyleneglycol methacrylic acid (TEGMA), 75.00 g of AP.H. glass filler, 0.50 g of camphorquinone and 0.50 g of propamine are mixed to form a dental restorative material. Visible light is applied to the dental restorative material to form a polymeric dental restorative having a Compressive strength of 139 (MPa), Flexural strength of 53 (MPa), Diametral tensile strength of 35 (MPa), Barcol hardness (# 934) of 86 and Polymerization shrinkage of 1.3%.

Dental Root Canal Filling Material

EXAMPLE 10

21.25 g of the macromonomer formed as described in Example 6, 5.32 g of TEGMA, 6.64 g of ethoxylated Bis-GMA, 66.45 g of calcium tungstate, 0.17 g of propamine and 0.17 g of dibenzylperoxide are mixed to form a dental root canal filing material which polymerizes with a setting time at 23° C. of 32 minutes setting time at 37° C. of 18 minutes, solubility of 0.3%, Radio-opacity of 9.2 mm Al and Polymerization shrinkage of 1.0%.

It should be understood that while the present invention has been described in considerable detail with respect to certain specific embodiments thereof, it should not be considered limited to such embodiments but may be used in other ways without departure from the spirit of the invention and the scope of the appended claims.

We claim:

1. A dental filling material, comprising: a filler and a α,ω-methacrylate terminated epoxide-carboxylic acid macromonomer compound formed by reaction of at least one diepoxide, at least one dicarboxylic acid and at least one unsaturated mono-carboxylic acid and having the general formula:

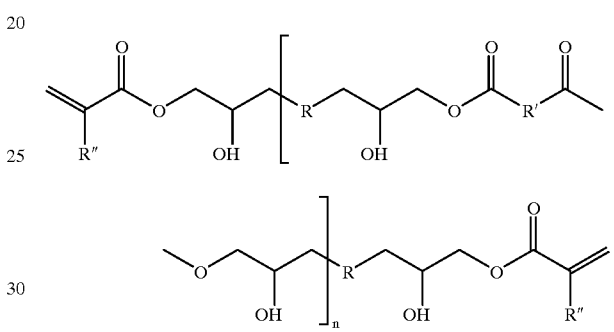

wherein R is an aromatic aliphatic or cycloaliphatic moiety formed from a diepoxide, R' is a substituted or unsubstituted aliphatic or cycloaliphatic moiety formed from a dicarboxylic acid, R" is hydrogen, a substituted or unsubstituted aliphatic, araliphatic, aromatic or cycloaliphatic moiety, and n is an integer from 1 to 20, said filler comprising a major portion of said material, and said material polymerizes with a polymerization shrinkage of less than about 1.3 volume percent.

2. The dental material of claim 1 wherein said filler comprises inorganic particles and said filler comprises a substantial portion of said material and said composition is a dental restorative, dental cement or dental luting material.

3. The dental filling material of claim 1 wherein said material polymerizes with a polymerization shrinkage of about 1 percent.

4. A dental restorative material comprising: a filler and a α,ω-methacrylate terminated epoxide-carboxylic acid macromonomer compound formed by reaction of at least one diepoxide, at least one dicarboxylic acid and at least one unsaturated mono-carboxylic acid and having the general formula:

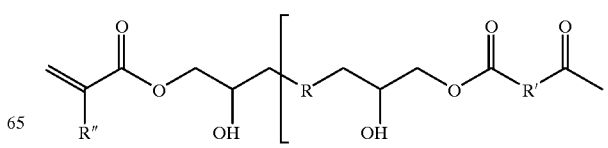

-continued

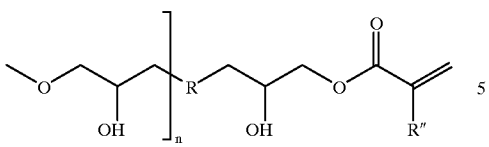

wherein R is an aromatic moiety formed from a diepoxide,
R' is a substituted or unsubstituted aliphatic or cycloaliphatic moiety formed from a dicarboxylic acid,
R" is hydrogen, a substituted or unsubstituted aliphatic, araliphatic, aromatic or cycloaliphatic moiety, and n is an integer from 1 to 20, said filler comprising a major portion of said material and said material polymerizes with a polymerization shrinkage of less than about 1.3 volume percent.

5. The dental restorative material of claim 4 wherein said material polymerizes with a polymerization shrinkage of about 1 percent.

6. A dental restorative composition comprising filler and α,ω-methacrylate terminated carboxylic acid macromonomer compound formed by reaction of at least one diepoxide, at least one dicarboxylic acid and at least one unsaturated mono-carboxylic acid and having the general formula:

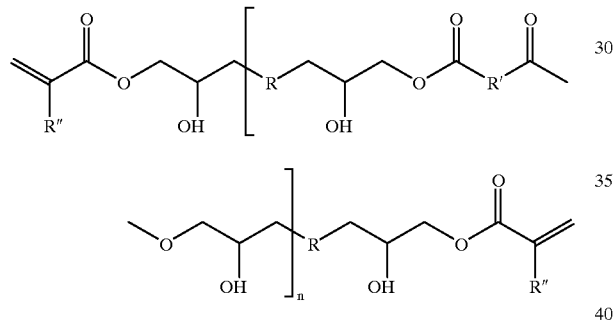

wherein each R independently is an aromatic, aliphatic or cycloaliphatic moiety formed from a diepoxide,
R' is a substituted or unsubstituted aliphatic or cycloaliphatic moiety formed from a dicarboxylic acid,
each R" independently is hydrogen, a substituted or unsubstituted aliphatic, araliphatic, aromatic or cycloaliphatic moiety and n is an integer from 1 to 20 and said material polymerizes with a polymerization shrinkage of less than about 1.3 volume percent.

7. The dental restorative composition of claim 6 wherein said composition polymerizes with a polymerization shrinkage of about 1 percent and said filler is an inorganic filler.

8. A dental cement composition comprising filler and a α,ω-methacrylate terminated carboxylic acid macromonomer compound formed by reaction of at least one diepoxide, at least one dicarboxylic acid and at least one unsaturated mono-carboxylic acid and having the general formula:

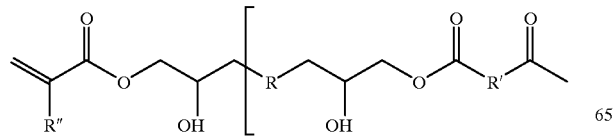

wherein each R independently is an aromatic, aliphatic or cycloaliphatic moiety formed from a diepoxide,
R' is a substituted or unsubstituted aliphatic or cycloaliphatic moiety formed from a dicarboxylic acid,
each R" independently is hydrogen, a substituted or unsubstituted aliphatic, araliphatic, aromatic or cycloaliphatic moiety, and n is an integer from 1 to 20 and said material polymerizes with a polymerization shrinkage of less than about 1.3 volume percent.

9. The dental cement composition of claim 8 wherein said composition polymerizes with a polymerization shrinkage of about 1 percent and said filler is an inorganic filler.

10. A dental luting material comprising filler and α,ω-methacrylate terminated carboxylic acid macromonomer compound formed by reaction of at least one diepoxide, at least one dicarboxylic acid and at least one unsaturated mono-carboxylic acid and having the general formula:

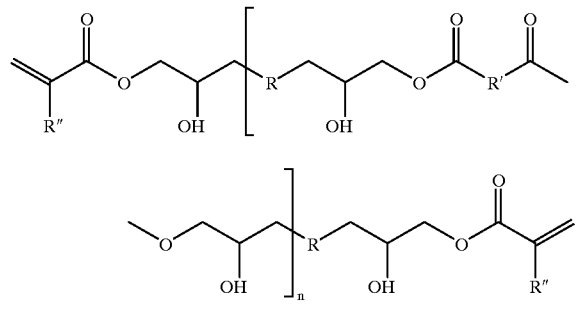

wherein each R independently is an aromatic, aliphatic or cycloaliphatic moiety formed from a diepoxide,
R' is a substituted or unsubstituted aliphatic or cycloaliphatic moiety formed from a dicarboxylic acid,
each R" independently is hydrogen, a substituted or unsubstituted aliphatic, araliphatic, aromatic or cycloaliphatic moiety, and n is an integer from 1 to 20 and said material polymerizes with a polymerization shrinkage of less than about 1.3 volume percent.

11. The material of claim 10 wherein said material polymerizes with a polymerization shrinkage of about 1 percent and said filler is an inorganic filler.

12. A dental restorative composition comprising filler and α,ω-methacrylate terminated carboxylic acid macromonomer compound formed by reaction of at least one diepoxide, at least one dicarboxylic acid and at least one unsaturated mono-carboxylic acid and having the general formula:

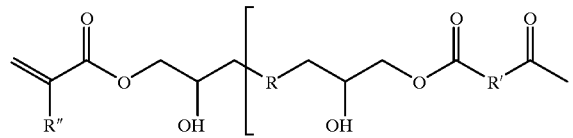

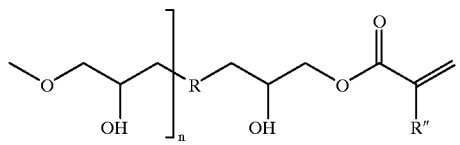
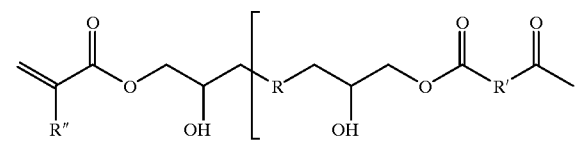

wherein each R independently is an aromatic, aliphatic or cycloaliphatic moiety formed from a diepoxide, R' is a substituted or unsubstituted aliphatic or cycloaliphatic moiety formed from a dicarboxylic acid, each R" independently is hydrogen, a substituted or unsubstituted aliphatic, araliphatic, aromatic or cycloaliphatic moiety, and n is an integer from 1 to 20 said composition being polymerizable with a polymerization shrinkage of about 1 percent to form a polymeric dental composite having a radioopacity of about 9.2 mm Al and a Barcol hardness of about 86.

13. A dental luting material comprising filler and α,ω-methacrylate terminated carboxylic acid macromonomer compound formed by reaction of at least one diepoxide, at least one dicarboxylic acid and at least one unsaturated mono-carboxylic acid and having the general formula:

wherein each R independently is an aromatic, aliphatic or cycloaliphatic moiety formed from a diepoxide, R' is a substituted or unsubstituted aliphatic or cycloaliphatic moiety formed from a dicarboxylic acid, each R' independently is hydrogen, a substituted or unsubstituted aliphatic, araliphatic, aromatic or cycloaliphatic moiety, and n is an integer from 1 to 20 and said composition being polymerizable with a polymerization shrinkage of about 1 percent to form a polymeric dental composite having a radioopacity of about 9.2 mm Al and a Barcol hardness of about 86.

* * * * *